United States Patent [19]

Guettler et al.

[11] Patent Number: 5,723,322
[45] Date of Patent: Mar. 3, 1998

[54] PROCESS FOR MAKING SUCCINIC ACID, MICROORGANISMS FOR USE IN THE PROCESS AND METHODS OF OBTAINING THE MICROORGANISMS

[75] Inventors: Michael V. Guettler, Holt; Mahendra K. Jain, Okemos, both of Mich.; Bhupendra K. Soni, Westmont, Ill.

[73] Assignee: Michigan Biotechnology Institute, East Lansing, Mich.

[21] Appl. No.: 584,597

[22] Filed: Jan. 11, 1996

Related U.S. Application Data

[62] Division of Ser. No. 359,370, Dec. 20, 1994, Pat. No. 5,504,004.

[51] Int. Cl.⁶ .................................. C12P 7/46; C12P 1/04; C12N 1/20

[52] U.S. Cl. .................. 435/145; 435/252.1; 435/822
[58] Field of Search ................ 435/145, 252.1, 435/822

[56] References Cited

U.S. PATENT DOCUMENTS

| | | | |
|---|---|---|---|
| 5,143,833 | 9/1992 | Datta et al. | 435/145 |
| 5,143,834 | 9/1992 | Glassner et al. | 435/145 |
| 5,504,004 | 4/1996 | Guettler et al. | 435/145 |

*Primary Examiner*—Herbert J. Lilling
*Attorney, Agent, or Firm*—Quarles & Brady

[57] ABSTRACT

A fermentation process for making succinic acid in high concentrations employs a bacteria obtained from the rumen contents of cattle. A preferred bacteria is Bacterium 130Z (ATCC No. 55618).

4 Claims, No Drawings

PROCESS FOR MAKING SUCCINIC ACID, MICROORGANISMS FOR USE IN THE PROCESS AND METHODS OF OBTAINING THE MICROORGANISMS

This is a division of application Ser. No. 08/359,370 filed Dec. 20, 1994 now U.S. Pat. No. 5,504,004.

FIELD OF THE INVENTION

This invention relates to a process for making succinic acid, microorganisms for use in the process and methods for obtaining these microorganisms.

BACKGROUND OF THE INVENTION

Succinic acid and its derivatives are widely used as specialty chemicals With applications in foods, pharmaceuticals, and cosmetics.

Commercial fermentations for other organic acids, such as citric and lactic acids, typically produce concentrations of 80 to 120 g/l. However, such fermentations for succinic acid usually produce much lower concentrations of less than 40 g/l.

The Glassher et al. U.S. Pat. No. 5,143,834 and the Datta et al. U.S. Pat. No. 5,168,055, disclose integrated processes for the production of succinic acid employing the anaerobic bacterium, *Anaerobiospirillum succiniciproducens,* which produces comparatively low concentrations of succinic acid of approximately 35 g/l.

Although succinic acid is a common intermediate in the metabolic pathway of several anaerobic microorganisms, such as Propionibacterium, no microorganisms are described in the literature which produce succinate in high concentrations. Well known species of rumen bacteria convert plant carbohydrates to fatty acids and to a very large extent succinic acid[1]. *Prevotella ruminicola* and *Ruminobacter amylophilus* are examples of well known species of rumen bacteria that produce major amounts of succinic acid but in generally low yields. Unfortunately, the typical rumen organisms cannot tolerate the presence of high concentrations of succinic acid or its salts and tend to lyse after comparatively short fermentation times which makes them unsuitable for industrial application. It appears that the accumulation of very high concentrations of acids, such as succinic acid, or their salts is not a normal phenomenon for microorganisms and it is damaging to them.

There is a need for a fermentation process for succinic acid which produces higher concentrations in the fermentation broth and which permit an economical recovery of succinic acid. It also would be advantageous to have microorganisms that can tolerate higher levels of succinic acid and its salts. It would be advantageous to have a method of obtaining this type of organism.

SUMMARY OF THE INVENTION

The objects of the invention are to disclose a novel process for making succinic acid in high concentrations, microorganisms that are useful in that process and a method for obtaining such microorganisms.

The method of the present invention for the production of succinic acid basically comprises, providing an aqueous fermentation medium containing a submerged culture of a microorganism and a source of assimilable carbon, such as a carbohydrate; and cultivating said organism under anaerobic conditions or aerobic conditions in the presence of carbon dioxide to form succinic acid in a concentration of at least about 50 g/l in said fermentation medium.

The novel microorganisms of the present invention are ionophore resistant species of rumen bacteria obtained from cattle. These species are more resistant to inhibition by succinic acid and produce a higher concentration of succinate in a fermentation process than can be obtained in a corresponding fermentation using other succinate producing species under otherwise identical conditions.

The preferred method of obtaining strains for use in the method of the present invention for producing succinic acid comprises growing bacteria from the rumen contents of cattle in an aqueous fermentation medium with disodium fumarate (about 5 g/l to about 30 g/l) and an antibiotic ionophore (about 8 mg/l to about 32 mg/l), which favors the growth of the succinate producing organisms; and, then isolating from the culture medium the colony of the strain which produces succinic acid in the highest concentration.

A preferred microorganism for use in the method is an isolated, biologically pure culture consisting essentially of Bacterium 130Z (ATCC No. 55618).

DETAILED DESCRIPTION OF PREFERRED EMBODIMENT

In the preferred practice of the present invention, a substantially pure culture of the Bacterium 130Z (ATCC 55618) is grown at a controlled pH between about 6.0 to about 7.2 in a fermentor on a medium containing a source of fermentable carbon containing a carbohydrate and other nutrients, such as corn steep liquor, under a partial pressure of at least about 0.1 atmosphere $CO_2$ until the fermentation broth contains at least about 50 g/l of succinic acid.

The source of fermentable carbon used in the practice of this invention can be any carbohydrate that is fermented by the strain of bacteria used. These carbohydrate sources include dextrose, sucrose, fructose, lactose, soluble starches, and corn syrups. The fermentation is conducted in an aqueous medium in the presence of dissolved carbon dioxide. Other nutrients and growth factors needed for the growth and the reproduction of the microorganism employed also are added to the medium.

The concentration of carbohydrate in the medium is between about 20 g/l to about 150 g/l, preferably between about 90 g/l and about 120 g/l. Carbohydrate concentrations above about 70 g/l give solutions with such high osmotic pressures that the organisms usually used to produce succinic acid do not grow well; however, the strains of the present invention will tolerate such conditions.

Carbon dioxide can be supplied to the fermentation medium in various ways. The medium can be sparged with $CO_2$ gas. The fermentation can be run in a pressurized reactor which contains carbon dioxide at superatmospheric pressure. The $CO_2$ can be mixed with other gases as long as the gases employed do not interfere with the growth and metabolism of the organism employed. Carbon dioxide can also be supplied to the fermentation medium by the addition of carbonates or bicarbonates which generate this gas under the conditions of the fermentation. The medium should contain dissolved $CO_2$ in equilibrium with a minimum of about 0.1 atmosphere partial pressure of carbon dioxide. In the preferred embodiment, the medium is saturated with carbon dioxide and the atmosphere contains about 0.3 atmosphere partial pressure of carbon dioxide or higher.

In order to obtain good production of succinate salt, the pH of the medium is maintained in the range of from about 7.2 to about 6.0. The pH is conveniently maintained by the addition of alkaline carbonates, alkaline earth hydroxides, or mixtures thereof.

The fermentation process of this invention is carried out at a temperature between about 25° C. and about 40° C. For example, the optimum growth of Bacterium 130Z is at about 38° C. Since it is a facultative anaerobe, fermentations using Bacterium 130Z can be carried out under either anaerobic conditions or in the presence of air and carbon dioxide in a medium which has been sterilized by heat or other means well known in the fermentation art.

The preferred Bacterium 130Z (ATCC No. 55618) has been demonstrated to be capable of producing high concentrations of succinic acid (about 50 to about 80 g/l) with a high productivity.

The Bacterium 130Z is obtained as previously described and as more specifically described in the description of the experimental work.

Materials and methods organism

The succinic acid producing strain Bacterium 130Z (ATCC No. 55618) was isolated in a Michigan Biotechnology Institute (MBI) laboratory from bacteria from the rumen contents of fistulated cattle. Other succinic acid producing organisms used for comparison purposes were *Anaerobiospirillum succiniciproducens* ATCC 53488, *Ruminobacter amylophilus* DSM 1361, *Succinivibrio dextrinosolvens* ATCC 19716, *Prevotella ruminocola* ATCC 19188 (American Type Culture Collection (ATCC), Rockville, Md.; German collection of Microorganisms and Cell Cultures (DSM), Braunschweig, Germany).

chemicals

Chemicals were obtained from Sigma Chemicals, St Louis Mo. or Aldrich Chemical, Milwaukee, Wis. unless otherwise stated. Gases and gas mixtures were supplied by Linde (Michigan Welding, East Lansing Mich.). For anaerobic conditions, oxygen was scrubbed out by passage over heated copper filings.

enrichment and isolation

Source: Rumen contents were collected from fistulated cattle on various feeding regimens. Samples were transported to MBI and transferred to vials for storage under nitrogen at 4° C.

Enrichment and isolation media: The standard salts (SS) were NaCl 1.0, $K_2HPO_4$ 3.0, $MgCl_2.6H_2O$ 0.2, $CaCl.2H_2O$ 0.2, $(NH_4)_2SO_4$ 1.0 g/l. For enrichments, 10 ml of SS was used with corn steep liquor (CSL) 20.0 g/l (Corn Products Corporation, Englewood Cliffs, N.J.). The same medium was used for isolation of pure cultures but with the following additions: $B_{12}$ 1 mg; biotin, folic acid 20 mg; thiamine, riboflavin, niacin, pantothenate, p-aminobenzoate, and lipoic acid 50 mg; $B_6$ 100 mg; sodium acetate 1.36 g; xylose 1 g; methyl butyrate, valerate, isobutyrate, isovalaerate 0.2 ml; 1,4-napthoquinone 10 mg; and hemin 500 mg/l. For plating Bacto yeast extract 5.0 g and Bacto peptone 10.0 g/l were substituted for the CSL and 100 ml was dispensed into vials containing 1.8 g of Bacto agar and 1.0 g of $MgCO_3$. All media were gassed and dispensed under $CO_2/N_2$ (5%/95%). Plates were poured in an anaerobic glove bag (Coy Inc, Ann Arbor, Mich.). Glucose or maltrin (20 g/l) was added as substrates to the enrichment and isolation media. Disodium fumarate (15 g/l) was added to the enrichment medium and plates for isolation. Stock solutions of Lasalocid (Sigma Chemical, St. Louis, Mo.), an antibiotic ionophore, were prepared in ethanol (10 mg/ml) and added to enrichment and isolation plates to give a concentration of 16 µg/ml.

Isolation and screening: An enrichment train was established with a 10% inoculum, and subcultures were made after 18 hours of incubation at 37° C. Samples from the third enrichment vials were diluted ($10^{-6}$) in phosphate buffered saline and 0.1 ml aliquots were spread on plates in the glove bag. Plates were incubated anaerobically in an Oxoid Anaerobic Jar (Oxoid Ltd., Basingstoke, England) with a 100% $CO_2$ atmosphere. After 24 to 48 hours single well isolated colonies were picked with a 22 gauge needle and washed into vials of glucose isolation medium. Primary isolates were grown 24–36 hours in CSL medium. Samples from each vial were analyzed by HPLC and screened for succinic acid production.

analysis

The organic acid fermentation products were determined using high-performance liquid chromatography (HPLC)[2]. A waters Model 600 HPLC system with a BioRad HPX-87H column and a Waters Model 410 Refractive Index detector were used in this analysis. Carbohydrate also was determined by the same HPLC methods. Peptone yeast glucose (PYG) fermentation product determination was by gas liquid chromatography[3].

biochemical

Enzymatic activities were determined with the Rapid Ana II System (Innovative Diagnostics, Atlanta, Ga.), with cells grown on Brain Heart Infusion (BBL, Cockeysville, Md.). The API CH50 (Analytab Products, Plainview, N.Y.) was done as directed using cells grown on Rabbit Blood Agar plates (BBL, Cockeysville, Md.), aerobically with extra $CO_2$. Cellular Fatty Acids were determined using the Microbial Identification System (MIDI, Newark, Del.) and software for anaerobic and aerobic bacteria. Cells were grown anaerobically in PYG and aerobically using Tripticase Soy Agar (BBL). Peptone yeast (PY) medium was made as described in the VPI manual[3].

The test for fumarate reduction was done in a manner of Hollander[4]. Pressure tubes (Belco Glass, Vineland, N.J.) with 10 ml of PBB medium was used. PBB medium contained NaCl 0.9, $MgCl_2.6H_2O$ 0.2, $CaCl_2.2H_2O$ 0.1, $NH_4Cl$ 1.0 g/l and resazurin 3, $CoCl_2.6H_2O$ 1.7, $FeSO_4.7H_2O$, $MnCl_2.4H_2O$, $CaCl_2.2H_2O$, $ZnCl_2$ 1.0, $Na_2SeO_3$ 0.17, $CuCl_2.2H_2O$ 0.2, $NiSO_4.6H_2O$ 0.26, $Na_2MoO_4$, $H_3BO_3$ 0.1 mg/l. Bacto yeast extract (1.2%) was added along with 0.2 ml phosphate buffer. The phosphate buffer was $KH_2PO_4$ 150 and $K_2HPO_4$ 290 g/l. A 0.1% inoculum was used and incubation was stationary at 37° C.

serum vial cultures

Serum vial culture technique was used and transfers were made by syringe(5). $MgCO_3$, 20–80 g/l, was added to the vials for pH maintenance. Carbon dioxide dependeny tests were done in 158 ml serum vials containing 50 ml of FB medium(6) and 1 ml phosphate buffer. All vials were incubated at 37° C. in a model G25 Incubator Shaker (New Brunswick Scientific, Edison, N.J.).

fermentation

One liter batch fermentations were conducted in 2-liter MultiGen fermenters (New Brunswick Scientific, Edison, N.J.). The temperature was controled at 39° C. Carbon dioxide was sparged at 0.05–0.1 volume/volume/minute. The culture was stirred at 300 rpm with flat blade turbine impellers. The pH was automatically controlled (Chemcadet, Cole Palmer, Chicago, Ill.) with the addition of 10N NaOH, or 5.5M $Na_2CO_3$, or combinations of NaOH and $Na_2CO_3$. The medium was SS plus CSL and/or yeast extract, with other additions and modifications as stated.

Results enrichment and isolation

Ionophore/fumarate enrichment vials produced high succinate concentrations and isolates from these enrichments produced succinate at concentrations greater than 30 g/l from glucose (Table 1). Concentrations over 30 g/l had not been seen with isolates from various other enrichment schemes from various environments including the rumen.

Initial isolates were obligate anaerobes that produced succinic acid concentrations higher than those produced by rumen species obtained from culture collections. For example, isolate R413 produced 31.2 g/l of succinic acid in a 1-liter fermenter and 37.9 in a 1-liter fedbatch reactor. They could initiate growth without added reducing agents and had other desirable properties but were not ideal because yield was lost to the production of lactate. A second class of isolates were facultative anaerobes typified by strain Bacterium 130Z. These strains did not produce lactate and produced succinic acid in a much higher yield than other rumen organisms and with the proper conditions Bacterium 130Z produced nearly 80 g/l succinic acid.

TABLE 1

Acids production by isolates from ionophore/fumarate enrichment.

| Isolate | Succinic | Lactate | Acetate | Formate | Pyruvate |
|---------|----------|---------|---------|---------|----------|
| R413    | 31.2(65.5)[1] | 14.3 | 6.6 | 0.7 | 0.0 |
| 130Z    | 44.4(83.7) | 0.0 | 4.1 | 1.4 | 6.4 |

[1]succinic acid yield (wt %)

Bacterium 130Z product concentration

The most distinguishing feature of Bacterium 130Z is its ability to produce very high succinic acid concentrations. Bacterium 130Z produced more than 60 g/l of succinic acid in less than 36 hours and accumulated 75–79 g/l with continued incubation. No other known strain produces concentrations this high (Table 2). Concentrations of nearly 80 g/l of succinic acid were obtained in serum vial cultures containing 15 g/l each of corn steep liquor and yeast extract, 100 g/l glucose, and 80 g/l of $MgCO_3$. The $(NH_4)_2SO_4$ was omitted.

TABLE 2

Succinic acid produced by different microbial cultures.

| Organism | Source | Succinic Acid (g/l) | Mode |
|----------|--------|---------------------|------|
| Bacterium 130Z | isolate[1],rumen | 79 | serum vial |
| Bacterium 130Z | isolate,rumen | 68 | batch fermenter |
| R413 | isolate,rumen | 37.9 | fed batch fermenter |
| A. succiniciproducens | ATCC 53488,dog | 37.6 | batch fermenter |
| Ruminobacter amylophilus | DSM 1361,rumen | 11.9 | batch fermenter |
| Succinivibrio dextrinosolvens | ATCC 19716,rumen | 26.7 | batch fermenter |
| Prevotella ruminocola | ATCC 19188,rumen | 18.9 | batch fermenter |

[1]Ionophore/fumarate enrichment isolates.

osmotolerance

Bacterium 130Z is tolerant to high succinate concentrations (Table 3). It grows in medium saturated with magnesium succinate and it produces succinic acid in this medium despite any kinetic or equilibrium disadvantage this presents. Bacterium 130Z produced succinic acid in a fermenter with an initial concentration of 49 g/l disodium succinate, producing a concentration over 100 g/l in 39 hours. Well known succinate producing strains do not tolerate product concentrations this high. A. succiniciproducens will not initiate growth in media containing 20 g/l disodium succinate.

TABLE 3

Tolerance to high succinate concentrations.

| | Initial Concentrations of Succinic Acid Salts | | |
|---|---|---|---|
| Organism | 49 g/l disodium | 96 g/l disodium | 130 g/l magnesium |
| 130Z | growth and fermentation | growth and fermentation | growth and fermentation |
| A. succiniciproducens | no growth | no growth | no growth | relationship to carbon dioxide

Bacterium 130Z is a capnophile. It requires an atmosphere enriched in carbon dioxide for rapid fermentative growth and development. Bacterium 130Z's response to carbon dioxide concentrations is related to its ability to make high concentrations of succinic acid. Carbon dioxide is a substrate in the succinate pathway and production of high concentrations of succinic acid causes a demand much higher than normal biosynthetic activity. This strain is dependent upon carbon dioxide supplementation for high succinate productivity.

relationship to nitrogen

Bacterium 130Z can obtain its nitrogen from organic sources. The normal concentration of ammonium sulfate in the CSL containing medium is 1 g/l. Growth of Bacterium 130Z and succinic acid production is increased by the elimination of the ammonium sulfate. Serum vial studies indicate a trend of increased succinate with the reduction of this salt (Table 4). Succinic acid concentrations of nearly 80 g/l were achieved in vials with the complete elimination of ammonium sulfate performance in 1-liter fermenters was also improved through the elimination of ammonium sulfate and the extent of the effect may vary from lot to lot of CSL. Excess ammonium ion limits succinic acid production to less than 30 g/l.

TABLE 4

Effect of 1 g/l ammonium sulfate on succinic acid prodution

| $(NH_4)_2SO_4$ (% of normal) | Succinic Acid Produced (% of normal) |
|---|---|
| 25 | 123 |
| 50 | 109 |

TABLE 4-continued

Effect of 1 g/l ammonium sulfate on succinic acid prodution

| (NH₄)₂SO₄ (% of normal) | Succinic Acid Produced (% of normal) |
|---|---|
| 100 | 100 |
| 150 | 87 |
| 200 | 79 | relationship to other nutrients

Bacterium 130Z grows fermentatively with glucose, some simple salts, and a small amount of yeast extract. It produces succinate and acetate as major products. The rate and extent of growth is markedly influenced by the addition of yeast extract and casein hydrolysate. An extreme example is a fermentation with 20 g/l yeast extract and 2 g/l of casein hydrolysate. Bacterium 130Z produced 41 g/l of succinic acid in 15 hours.

Corn steep liquor (CSL), a byproduct of the corn wet milling industry, is an important fermentation medium constituent. The succinic acid yield (wt %) is improved by using a CSL based medium with an optimal amounts of yeast extract to stimulate rapid growth and fermentation. Nutrient sources can be combined to provide a high fermentation rate, high concentration, and high yield. Acids production by Bacterium 130Z is tractable by nutrient manipulation and responsive to optimization efforts. Yeast extract and casein hydolysate speed up the fermentation and increase succinate concentration. CSL has the effect of improving succinate yields. Optimum combinations can be arrived at empirically and maybe varied to obtain the best economic results. High concentration and high yield are the results of using 20 g/l CSL and 1 g/l of yeast extract, the same results were obtained 10 hours sooner with 10 g/l CSL and 6 g/l yeast extract (Table 5).

TABLE 5

Effect of nutrient on productivity.

| Time (hrs) | Corn steep liquor (%) | Yeast extract (%) | Succinic acid (g/l) | Yield (wt %) |
|---|---|---|---|---|
| 39.3 | 2 | 0.1 | 46.2 | 83 |
| 29.5 | 1 | 0.6 | 45.8 | 83 | relationship to oxygen

Bacterium 130Z is a facultative anaerobe that has a fermentative metabolism. It is not sensitive to oxygen exposure as is *A. succiniciproducens* and other obligate anaerobes (Table 6). Fermentation media for Bacterium 130Z can be prepared in the standard manner without any special effort to exclude oxygen. Bacterium 130Z is tolerant to protracted exposures to air and will grow well in the presence of air if it is supplied with an increased partial pressure of $CO_2$.

TABLE 6

Growth[1] and fermentation after 60 minutes exposure to air.

| Organism | Before | After |
|---|---|---|
| Bacterium 130Z | + | + |
| *Anaerobiospirillum succiniciproducens* ATCC 53488 | + | − |
| *Prevotella ruminicola* ATCC 19188 | + | − |

TABLE 6-continued

Growth[1] and fermentation after 60 minutes exposure to air.

| Organism | Before | After |
|---|---|---|
| *Ruminobacter amylophilus* DSM 1361 | + | − |
| *Succinivibrio dextrinisolvens* ATCC 19188 | + | − |

[1]Growth in anaerobically prepaared media.

relationship to substrate

Bacterium 130Z can grow and produce succinic acid in aqueous media containing more than 150 g/l dextrose, thus demonstrating an exceptional tolerance to high substrate concentrations and to unfavorable osmotic conditions. *A. succiniciproducens* does not grow in media containing over 70 g/l. Media containing 20 to 120 g/l dextrose are suitable for succinic acid production (Table 7). This organism also produces succinic acid from sucrose, lactose and byproducts such as whey.

TABLE 7

Growth and succinic acid production with different substrate concentrations.

| | Initial Dextrose (g/l) | | |
|---|---|---|---|
| Organism | 50 | 85 | 100 |
| Bacterium 130Z | 41 | 65 | 79 |
| *A. succiniciproducens* | 38 | ng[1] | ng[1] |

[1]no growth relationship to pH succinic acid production

Succinic acid production by *A. succiniciproducens* is markedly affected by slight shifts in pH (Table 8). In contrast, Bacterium 130Z is tolerant to a wider range of pH and therefore does not require strict pH control. A pH of 6.2 to 7.0 is generally satisfactory for high succinate production and yield (Table 8).

TABLE 8

Effect of PH on product formation.

| | Grams of Succinic Acid Produced[1] | |
|---|---|---|
| pH ± 0.1 | 130Z[2] | *A. succinicidproducens* |
| 6.2 | 50.8 | 43.5 |
| 6.8 | 56.6 | 20.2 |
| 7.2 | 41.8 | 14.7 |

[1]Calculated amount based on 1000 ml of fermentation medium.
[2]Various nutrient conditions were employed and no pH optimum is implied.

magnesium neutralization

Succinic acid can be produced through fermentation using magnesium carbonate for neutralization and pH maintenance. Media containing 80 g/l of magnesium carbonate can be used to produce 80 g/l succinic acid concentrations.

sodium neutralization

Succinic acid can be prepared through fermentation using sodium hydroxide or sodium carbonate solutions for acid neutralization. The use of $Na^+$ ion is desirable in a succinic acid process with recovery based on water splitting electrodialysis. Solutions of $NaCO_3$ or NaOH were employed for pH control with many Bacterium 130Z fermentations and both sodium salts were satisfactory for pH control. The sodium neutralized fermentations of Bacterium 130Z and *A. succiniciproducens* are compared in Table 9.

TABLE 9

Comparison of sodium neutralized fermentations.

| | Time (hrs) | Succinic acid (g/l) | Yield wt (%) |
|---|---|---|---|
| Bacterium 130Z | 29.5 | 45.8 | 83 |
| A. succiniciproducens | 29.5 | 34.1 | 87 |

130Z: 1% CSL, 0.6% YE and 2 g/l $MgCO_3$. Neutralization was with 10 N NaOH; *A. succiniciproducens*: 2% CSL, and tryptophan 25 ppm. Neutralization was with 5.5 M $NaCO_3$.

pH tolerance

A 10N solution of NaOH was used for neutralization in many Bacterium 130Z fermentations. In both the 0.3 and 1.0 liter fermenters, dosing with 10N NaOH results in momentary pH heterogeneity, but Bacterium 130Z was tolerant of pH control with 10N NaOH even in these small vessels. Bacterium 130Z was also tolerant of pH upsets. When alkali flow was interrupted overnight the pH desended to pH 5.1, Bacterium 130Z grew and consumed an additional 44 grams of dextrose after control was reestablished.

Description of Bacterium 130Z

Bacterium 130Z

Bacterium 130Z is a novel succinate producing strain with properties superior to any currently described, and it supplants *A. succiniciproducens* in an evolving succinic acid fermentation process. The most salient feature of this organism is that it produces large amounts of succinate from glucose and other carbohydrates. Over 93 g/l of magnesium succinate was produced from glucose in serum vials and 73 g/l of disodium succinate was produced in a 1-liter fermentor. Bacterium 130Z is remarkably tolerant to high succinic acid salt concentrations. It will grow and produce succinate in a medium containing 96 g/l disodium succinate and it will grow in a medium saturated with 130 g/l magnesium succinate. Bacterium 130Z produces succinate over a wider range of pH than *A. succiniciproducens*. The rate and efficiency with which carbohydrate is converted to succinate is flexible and can be controlled by changes in the medium. Succinic acid yields of 83–87 (wt %) have been attained.

Morphology

In CSL containing media Bacterium 130Z produces bacillary or coccobacillary forms. Bacterium 130Z is Gram negative. It produces nonmotile, nonsporeforming, pleomorphic rods. In rapidly growing cultures cells were smaller, had a regular rod shape, and were sometimes seen in short chains of four to six cells. Growth on glucose plating media was rapid and colonies were yellowish with a frosted glass appearance.

Growth and metabolic products

Bacterium 130Z is a chemoorganotoph. It grows on many common heterotrophic media. It grew rapidly at 37°–39° C.

Succinic and acetic acids are produced as the major metabolic products after 48 hours growth in PYG medium. Approximately 30 meg/l of succinic acid and 10 meg/l of acetic acid are produced in this poorly buffered medium. Small amounts of pyruvic and formic acid are also produced along with a trace of oxalacetic acid. NaCl (0.5%) stimulates the growth of Bacterium 130Z in PYG. Bacterium 130Z grows fermentatively in PY medium by utilizing 11 different carbohydrates (Table 10). Cultures of Bacterium 130Z remained viable for up to 1 month at 4° C.

TABLE 10

Growth and non-growth substrates for Bacterium 130Z.

| | Carbohydrates |
|---|---|
| growth | arabinose, fructose, galactose, glucose, lactose, maltose, mannitol, mannose, sucrose, xylose, salicin. |
| nongrowth | inositol, melibiose, rhamnose, raffinose, trehalose |

Fumerate reduction

The fumarate reductase test follows changes in turbidity in a medium containing fumarate but lacking carbohydrate (Table 11). It is a measurement of the terminal step in the succinate pathway and the results indicate the presence of strong fumarate reductase system in Bacterium 130Z.

TABLE 11

Growth response with disodium fumarate.

| Incubation time | Growth with[1] | |
|---|---|---|
| hours | 50 mM | none |
| 0 | 0.03 | 0.02 |
| 8.5 | 0.62 | 0.02 |
| 15.25 | 0.95 | 0.02 |
| 25 | 0.64 | 0.03 |

[1]600 nM

Biochemical

Based on Rapid AnaII, arginine aminopeptidase was present. Leucine, glycine, proline, phenylalanine, and serine aminopeptidase were absent. Arabinosidase, disaccharidase, β-galactosidase, α-glucosidase, β-glucosidase, α-galactosidase, α-fucosidase, acetyl-β-glucosaminidase, phosphatase, pyroglutamic acid arylamidase, tryptophanase (indole), and urease were absent.

Based on the API CH50 biotype, Bacterium 130Z is biochemically very reactive and produces acid from the degradation of 27 of 49 substrates (Table 12).

TABLE 12

| API 49 carbohydrate profile. CH50. | | | | | |
|---|---|---|---|---|---|
| 0 CONTROL | − | 18 MANNITOL | − | 36 STARCH | + |
| 1 GLYCEROL | + | 19 SORBITOL | + | 37 GLYCOGEN | + |
| 2 ERYTHRITOL | − | 20 a METHYL MANNOSIDE | − | 38 XYLITOL | − |
| 3 D ARABINOSE | − | 21 a METHYL GLUCOSIDE | − | 39 GENTIOBIOSE | + |
| 4 L ARABINOSE | + | 22 N ACETYL GLUCOSAMINE | + | 40 D TURANOSE | − |

TABLE 12-continued

API 49 carbohydrate profile. CH50.

| | | | | | |
|---|---|---|---|---|---|
| 5 RIBOSE | + | 23 AMYGDALIN | + | 41 D LYXOSE | − |
| 6 D XYLOSE | + | 24 ARBUTIN | + | 42 D TAGATOSE | − |
| 7 L XYLOSE | − | 25 ESCULIN | + | 43 D FUCOSE | − |
| 8 ADONITOL | + | 26 SALICIN | + | 44 L FUCOSE | − |
| 9 b METHYL XYLOSIDE | − | 27 CELLOBIOSE | + | 45 D ARABITOL | + |
| 10 GALACTOSE | + | 28 MALTOSE | + | 46 L ARABITOL | − |
| 11 GLUCOSE | + | 29 LACTOSE | + | 47 GLUCONATE | + |
| 12 FRUCTOSE | + | 30 MELIBIOSE | − | 48 2 KETO GLUCONATE | − |
| 13 MANNOSE | + | 31 SUCROSE | + | 49 5 KETO GLUCONATE | + |
| 14 SORBOSE | − | 32 TREHALOSE | + | | |
| 15 RHAMNOSE | − | 33 INULIN | − | | |
| 16 DULCITOL | − | 34 MELEZITOSE | − | | |
| 17 INOSITOL | − | 35 RAFFINOSE | + | | |

Cellular fatty acids and DNA base composition

Bacterium 130Z produced a very restricted pattern of cellular fatty acids (Table 13). Hydroxylated and nonhydroxylated long chain fatty acid methyl esters are present in whole-cell methanolysates. The predominant fatty acids were hexadecenoic acid ($C_{16:1}$) and hexadecanoic ($C_{16:0}$). Large amounts Of hydroxylated fatty acid are typical of Gram negative bacteria and 3-hydroxytetradecanoic (3OH—$C_{14:0}$) was present in Bacterium 130Z along with the straight chain tetradecanoic acid ($C_{14:0}$).

TABLE 13

Cellular fatty acid profile of Bacterium 130Z

| | % area |
|---|---|
| 16:1 CIS 9 FAME | 32.90 |
| 16:0 FAME | 32.75 |
| 14:0 FAME | 18.80 |
| 14:0 3OH FAME | 13.00 |
| 18:1 c11/t9/t6 FAME | 2.56 |

The DNA determined by an HPLC method[7] was 44.7–45.5 mol. % G+C.

In the method of the present invention for obtaining a ionophore resistant microorganism (such as Bacterium 130Z) the medium which is employed favors the growth of succinate producing organisms while inhibiting those producing other acids such as butyrate. How the medium works is not completely understood. However, the medium should contain the following:

1. Disodium fumarate, to give an energetic advantage to the rumen organisms with a strong pathway to succinate. In the final step of the pathway, fumarate is reduced to succinate and energy is conserved as ATP.

2. An antibiotic ionophore, such as Lasalocid, which is used commercially to increase feed efficiency in cattle on high energy diets and which selects for organisms that increase propionic acid in the rumen.

3. Dissolved carbon dioxide, a catabolic substrate in the succinate pathway.

4. $MgCO_3$, to allow the growth of acidogenic strains by maintaining pH and providing a continuous supply of $CO_2$/$HCO_3^-$.

5. Carbohydrate, to obtain strains able to utilize the desired feed stock for succinic acid production.

The preferred medium does not merely obtain the well known rumen organisms, it allows the development and isolation of organisms that produce succinate concentrations higher than those previously described for any organism.

It will be apparent to those skilled in the art that a number of changes and modifications can be made without departing from the spirit and scope of the invention. Therefore, it is intended that the invention only be limited by the claims.

References

1. Stewart, C. S., and M. P. Bryant. 1988. The Rumen Bacteria. In *The Rumen Microbial Ecosystem*. P. N. Hobson (ed.). Elsevier, London. pp. 21–75.

2. Guerrant et al. (1982). J. Clinical. Microbiol., 16:355

3. Holdeman, L. V., E. P. Cato, W. E. C. Moore (eds). (1977). Anaerobe Laboratory Manual, 4th ed. Blackburg, Virginia Polytechnic Institute and State University 4. Hollander, R. A. Hess-Reihse, and W. Mannheim. 1981. Respiratory quinones in Haemophilus, Pasteurella and Actinobacillus: Pattern, Function, and Taxonomic Evaluation. In Haemophilus, Pasteurella and Actinobacillus. M. Kilian, . . . (eds.). Academic Press, London. pp. 92–93

5. Miller, T. L., and M. J. Wolin. (1974). A serum bottle modification of the hungate technique for cultivating obligate anaerobes. Appl. Microbiol. 27:985–987

6. Woskow, S. A. and B. A. Glatz. 1991. Propionic acid production by a propionic acid-tolerant strain of *Propionibacterium acidipropionici* in batch and semicontinuous fermentation. Appl. Environ. Microbiol. 57: 2821–2828.

7. Mesbah, M., U. Premachandran, and W. B. Whitman. 1989. Precise Measurement of the G+C Content of Deoxyribonucleic Acid by High-Preformance Liquid Chromatography. Int. J. Syst. Bacteriol. 39:159–167.

8. Sutter, V. L., D. M. Citron, M. Edelstein, S. M. Finegold. 1986. *Wadsworth Anaerobic Bacteriology Manual*. Star Publishing, Belmont, CA pp. 71–78

We claim:

1. In the method of preparing succinic acid by the fermentation of a medium containing fermentable carbon employing a succinic acid producing microorganism, the improvement which comprises employing as the microorganism an ionophore resistant, rumen, bacteria that tolerates and grows in medium containing concentrations of succinate salts in excess of about 50 g/l.

2. The method of claim 1 in which the microorganism has all the identifying characteristics of Bacterium 130Z ATCC No. 55618.

3. The method of claim 1 in which the microorganism is a strain of a succinic acid producing Gram negative bacteria obtained from the rumen contents of cattle, said strain having been obtained by growing a parent strain in a culture medium containing fumarate and an antibiotic ionophore and isolating the strain from the culture medium.

4. A method for the production of succinic acid which comprises, providing an aqueous fermentation medium containing a culture of a microorganism and a source of fermentable carbon; and cultivating said organism under anaerobic or oxygen limited conditions in the presence of carbon dioxide to form succinic acid in a concentration of at least about 50 g/l in said fermentation medium;

wherein said organism is a strain of succinic acid producing bacteria that tolerates levels of succinic acid salts in excess of 30 g/l, which strain was obtained by growing bacteria from the rumen contents of cattle in an aqueous fermentation medium containing fumarate and an antibiotic ionophore, which favors the growth of succinate producing organisms.

* * * * *